US009636710B2

(12) United States Patent
Matsumoto et al.

(10) Patent No.: US 9,636,710 B2
(45) Date of Patent: *May 2, 2017

(54) ULTRASOUND ELEMENT AND ULTRASOUND ENDOSCOPE

(71) Applicants: OLYMPUS MEDICAL SYSTEMS CORP., Tokyo (JP); OLYMPUS CORPORATION, Tokyo (JP)

(72) Inventors: Kazuya Matsumoto, Nagano (JP); Kazuhisa Karaki, Shiojiri (JP); Mamoru Hasegawa, Nagano (JP); Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 686 days.

This patent is subject to a terminal disclaimer.

(21) Appl. No.: 14/152,058

(22) Filed: Jan. 10, 2014

(65) Prior Publication Data

US 2014/0128741 A1    May 8, 2014

Related U.S. Application Data

(63) Continuation of application No. PCT/JP2012/063793, filed on May 29, 2012.

(30) Foreign Application Priority Data

Jul. 11, 2011 (JP) ................................. 2011-153277

(51) Int. Cl.
  *A61B 8/00* (2006.01)
  *B06B 1/06* (2006.01)
  (Continued)

(52) U.S. Cl.
  CPC .............. *B06B 1/0622* (2013.01); *A61B 8/12* (2013.01); *A61B 8/445* (2013.01); *A61B 8/4483* (2013.01); *B06B 1/0292* (2013.01)

(58) Field of Classification Search
  CPC .... A61B 8/14; A61B 8/00; A61B 8/12; G01B 17/06
  See application file for complete search history.

(56) References Cited

U.S. PATENT DOCUMENTS

| 8,047,995 B2 | 11/2011 | Wakabayashi et al. |
| 2003/0006481 A1 | 1/2003 | Miyada et al. |

(Continued)

FOREIGN PATENT DOCUMENTS

| CN | 1820191 A | 8/2006 |
| CN | 101378605 A | 3/2009 |

(Continued)

OTHER PUBLICATIONS

Extended Supplementary European Search Report dated Mar. 9, 2015 from related European Application No. 12 81 1508.6.

(Continued)

*Primary Examiner* — Joel Lamprecht
(74) *Attorney, Agent, or Firm* — Scully, Scott, Murphy & Presser, P.C.

(57) ABSTRACT

An ultrasound element includes a silicon substrate, a lower electrode layer that has a plurality of lower electrode sections, and a plurality of lower wiring sections, and is connected to a lower electrode terminal to which a drive signal and a bias signal are applied, a lower insulating layer, an upper insulating layer in which a plurality of cavities smaller than the respective lower electrode sections are formed, an upper electrode layer that has a plurality of upper electrode sections that are disposed to face the respective lower electrode sections via the respective cavities, and are smaller than the lower electrode sections and larger than the cavities, and a plurality of upper wiring sections, and is connected to an upper electrode terminal at a ground potential that detects a capacitance signal, and a protection layer.

8 Claims, 10 Drawing Sheets

(51) Int. Cl.
    *A61B 8/12*     (2006.01)
    *B06B 1/02*     (2006.01)

(56) References Cited

U.S. PATENT DOCUMENTS

| | | |
|---|---|---|
| 2006/0179640 A1 | 8/2006 | Machida et al. |
| 2008/0067895 A1 | 3/2008 | Adachi et al. |
| 2009/0058228 A1 | 3/2009 | Wakabayashi et al. |
| 2009/0076393 A1 | 3/2009 | Adachi et al. |
| 2011/0154649 A1 | 6/2011 | Masaki |
| 2014/0121526 A1* | 5/2014 | Matsumoto .............. A61B 8/12 600/459 |

FOREIGN PATENT DOCUMENTS

| | | |
|---|---|---|
| EP | 1 837 087 A2 | 9/2007 |
| EP | 1 897 498 A1 | 3/2008 |
| EP | 1 992 290 A1 | 11/2008 |
| EP | 2030698 A1 | 3/2009 |
| JP | 2006-333952 A | 12/2006 |
| JP | 2007-229327 A | 9/2007 |
| JP | 2007-301023 A | 11/2007 |
| JP | 2009-050560 A | 3/2009 |
| JP | 2011-135408 A | 7/2011 |
| WO | WO 2006129525 A1 | 12/2006 |
| WO | WO 2007099696 A1 | 9/2007 |

OTHER PUBLICATIONS

International Search Report dated Jul. 17, 2012 issued in PCT/JP2012/063793.

\* cited by examiner

ULTRASOUND ELEMENT AND ULTRASOUND ENDOSCOPE

CROSS REFERENCE TO RELATED APPLICATION

This application is a continuation application of PCT/JP2012/063793 filed on May 29, 2012 and claims benefit of Japanese Application No. 2011-153277 filed in Japan on Jul. 11, 2011, the entire contents of which are incorporated herein by this reference.

BACKGROUND OF THE INVENTION

1. Field of the Invention

The present invention relates to an electrostatic capacitance type ultrasound element, and an ultrasound endoscope including the ultrasound element.

2. Description of the Related Art

An ultrasound diagnostic method by which an inside of a body is irradiated with ultrasound to image a state of the inside of the body from an echo signal for diagnosis comes into widespread use. One of the ultrasound diagnostic apparatuses for use in the ultrasound diagnostic method is an ultrasound endoscope (hereinafter called a "US endoscope"). In a US endoscope, an ultrasound transducer is placed at a distal end rigid portion of an insertion portion that is introduced into a body. An ultrasound transducer has a function of converting an electric signal into ultrasound, transmitting the ultrasound into a body, and receiving the ultrasound reflected at the inside of the body to convert the ultrasound into an electric signal.

So far, for ultrasound transducers, ceramics piezoelectric materials containing lead having a large environmental load, for example, PZT (lead zirconate titanate) has been mainly used. In contrast with this, Caronti et al. discloses an electrostatic capacitance ultrasound transducer (capacitive micromachined ultrasonic transducer; hereinafter called a "c-MUT") that is produced with use of a MEMS (micro electro mechanical systems) technique, and does not contain lead in the material. A c-MUT has an ultrasound cell (hereinafter, called a "US cell") in which an upper electrode section and a lower electrode section are disposed to face each other via a void portion (cavity), as a unit element. A plurality of US cells with respective electrode sections connected by wiring sections are arranged, and an ultrasound element (hereinafter, called a "US element") is configured.

The US cell vibrates a membrane (a vibration portion) including the upper electrode section by an electrostatic force by applying a voltage to between the lower electrode section and the upper electrode section, and generates ultrasound. When ultrasound enters from an outside, a space between both the electrodes changes, and therefore, the ultrasound is converted into an electric signal from a change of an electrostatic capacitance.

The US cell has a structure in which a plurality of functional layers are stacked. Therefore, if the placement positions of patterns of upper and lower functional layers are misaligned, the characteristics are impaired. For example, if the lower electrode section and the upper electrode section are not placed in correct positions, the areas of the electrodes facing each other, in other words, effective electrode areas likely decrease.

Japanese Patent Application Laid-Open Publication No. 2007-301023 discloses a c-MUT in which the size of an upper electrode section is smaller than the size of a cavity.

In the aforementioned c-MUT, the size of the upper electrode section is small, and therefore, the areas of the electrode sections facing each other are small, but even if the formation position of the upper electrode section is misaligned, the effective electrode areas do not change as long as the upper electrode section is located in a directly upper portion of the cavity.

SUMMARY OF THE INVENTION

An ultrasound element of an embodiment of the present invention includes a base substrate, a lower electrode layer that has a plurality of lower electrode sections, and a plurality of lower wiring sections that connect the plurality of lower electrode sections, and is connected to a lower electrode terminal to which a drive signal and a bias signal are applied, a lower insulating layer, an upper insulating layer in which a plurality of cavities smaller than the respective lower electrode sections are formed, an upper electrode layer that has a plurality of upper electrode sections that are disposed to face the respective lower electrode sections via the respective cavities, and are smaller than the lower electrode sections and larger than the cavities, and a plurality of upper wiring sections that connect the plurality of upper electrode sections, and is connected to an upper electrode terminal at a ground potential that detects a capacitance signal, and a protection layer.

Further, an ultrasound endoscope of another embodiment of the present invention has an ultrasound element including a base substrate, a lower electrode layer that has a plurality of lower electrode sections, and a plurality of lower wiring sections that connect the plurality of lower electrode sections, and is connected to a lower electrode terminal to which a drive signal and a bias signal are applied, a lower insulating layer, an upper insulating layer in which a plurality of cavities smaller than the respective lower electrode sections are formed, an upper electrode layer that has a plurality of upper electrode sections that are disposed to face the respective lower electrode sections via the respective cavities, and are smaller than the lower electrode sections and larger than the cavities, and a plurality of upper wiring sections that connect the plurality of upper electrode sections, and is connected to an upper electrode terminal at a ground potential that detects a capacitance signal, and a protection layer.

DETAILED DESCRIPTION OF THE PREFERRED EMBODIMENTS

Hereinafter, an ultrasound element 20 of a first embodiment, and an ultrasound endoscope 2 having the ultrasound element 20 will be described with reference to the drawings.
<Configuration of Ultrasound Endoscope>

Figure 1:
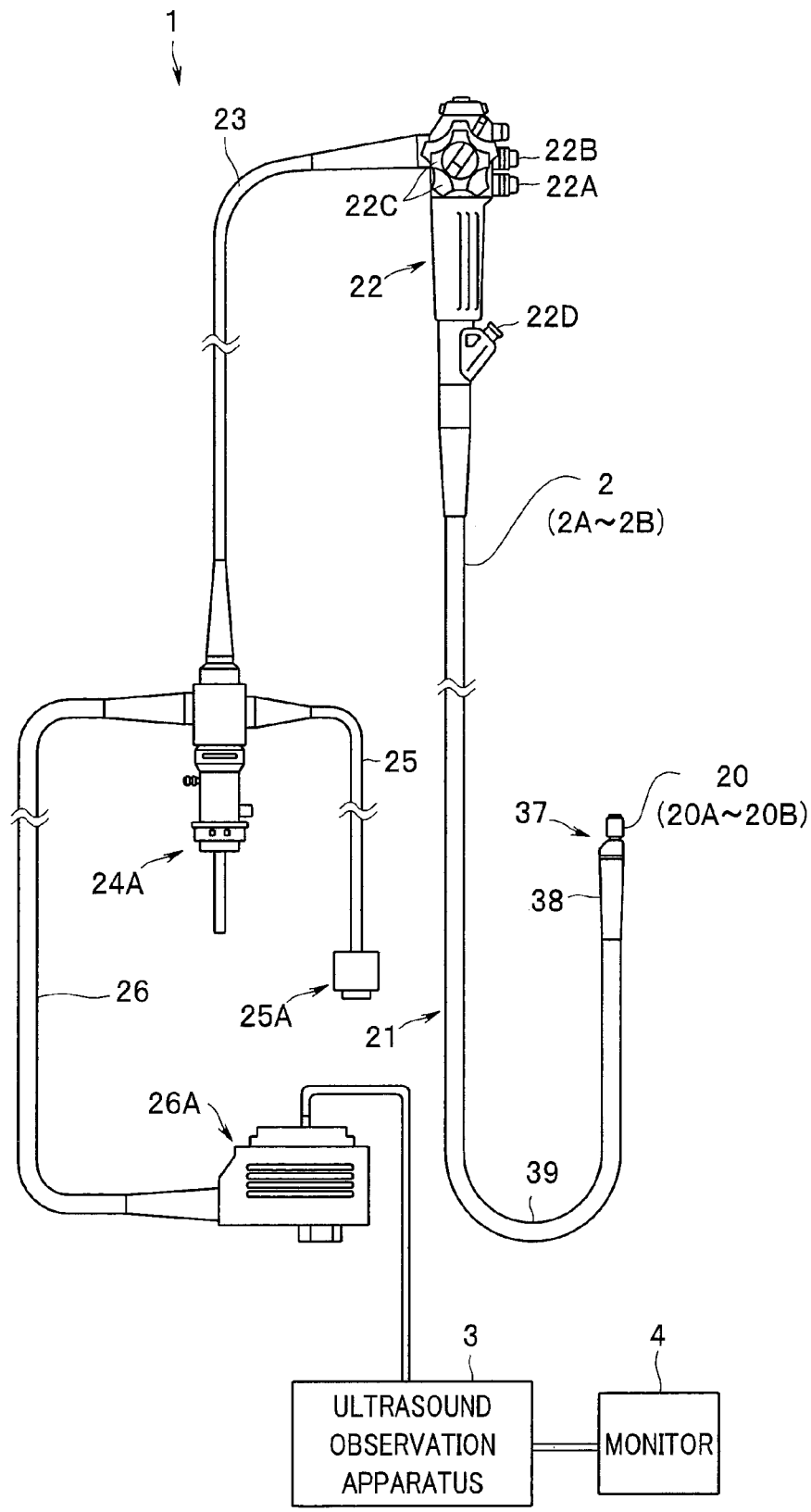
FIG. 1 is an external view for explaining an ultrasound endoscope of a first embodiment.

As shown in FIG. 1, a US endoscope 2 configures an ultrasound endoscope system 1 with an ultrasound observation apparatus 3 and a monitor 4. The US endoscope 2 includes an elongated insertion portion 21 that is inserted into a body, an operation portion 22 that is placed at a proximal end of the insertion portion 21, and a universal cord 23 that is extended from a side portion of the operation portion 22.

At a proximal end portion of the universal cord 23, a connector 24A that is connected to a light source apparatus (not illustrated) is placed. From the connector 24A, a cable 25 that is detachably connected to a camera control unit (not illustrated) via a connector 25A, and a cable 26 that is detachably connected to the ultrasound observation apparatus 3 via a connector 26A are extended. The monitor 4 is connected to the ultrasound observation apparatus 3.

The insertion portion 21 is configured by being connectively provided with a distal end rigid portion (hereinafter, called a "distal end portion") 37, a bending portion 38 that is located at a rear end of the distal end portion 37, and a flexible tube portion 39 that is located at a rear end of the bending portion 38 to reach the operation portion 22, has a small diameter, a long length and flexibility, in sequence from a distal end side. At a distal end side of the distal end portion 37, an ultrasound unit 30 is placed.

In the operation portion 22, an angle knob 22A that performs bending control of the bending portion 38 to a desired direction, an air feeding/water feeding button 22B that performs an air feeding and a water feeding operations, a suction button 22C that performs a suction operation, a treatment instrument insertion port 22D that is an inlet port for a treatment instrument that is introduced into a body and the like are placed.

Figure 2:
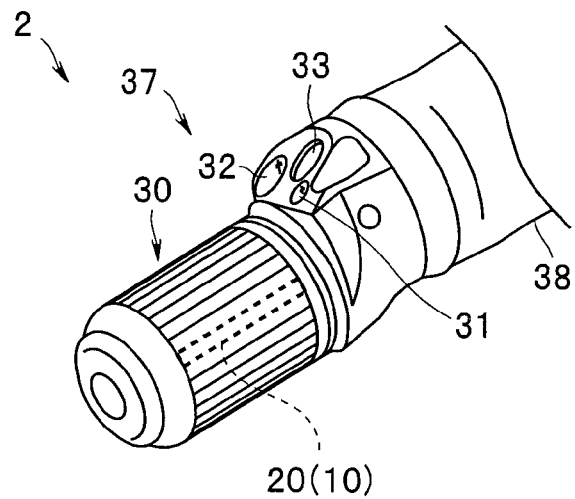
FIG. 2 is a perspective view for explaining a distal end portion of the ultrasound endoscope of the first embodiment.

As shown in FIG. 2, in the distal end portion 37 in which the ultrasound unit (US unit) 30 is provided, an illumination lens cover 31 that configures an illumination optical system, an observation lens cover 32 of an observation optical system, a forceps port 33 that is also used as a suction port, and an air feeding/water feeding nozzle not illustrated are placed.

Figure 3:
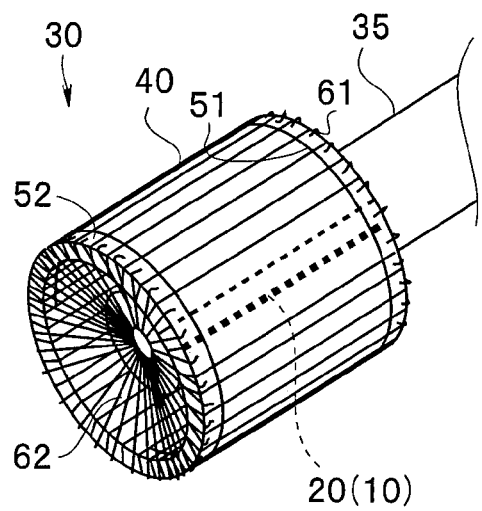
FIG. 3 is a perspective view for explaining a configuration of an ultrasound array at the distal end portion of the ultrasound endoscope of the first embodiment.

As shown in FIG. 3, an ultrasound array (US array) 40 of the US unit 30 is a radial type transducer group in which long sides of a plurality of ultrasound elements 20 rectangular in plain view are connected and roundly disposed in a cylinder shape. Namely, in the US array 40, 200 of US elements 20 each with a short side of 0.1 mm or less are placed in a direction of 360 degrees on a side surface of a cylinder with a diameter of 2 mm, for example. Note that the US array 40 is a radial type transducer group, but the US array may be a convex type transducer group that is folded into a convex shape.

At an end portion of the ultrasound array 40 in a cylindrical shape, a plurality of lower electrode terminals 52 are arranged, and are respectively connected to respective signal lines 62 of a coaxial cable bundle 35. Further, at the other end portion of the ultrasound array 40, a plurality of upper electrode terminals 51 are arranged. The upper electrode terminals 51 are respectively connected to respective capacitance detection lines 61 of the coaxial cable bundle 35. Namely, the coaxial cable bundle 35 includes coaxial cables having the same number of core wires as a total number of a plurality of signal lines 62 and a plurality of capacitance detection lines 61.

The coaxial cable bundle 35 is inserted through the distal end portion 37, the bending portion 38, the flexible tube portion 39, the operation portion 22, the universal cord 23 and the ultrasound cable 26, and is connected to the ultrasound observation apparatus 3 via the ultrasound connector 26A.
<Configuration of Transmission and Reception Section>

Next, with use of FIG. 4, FIG. 5 and FIG. 6, configurations of the US element 20 and an ultrasound cell (US cell) 10 will be described. Note that the drawings are all schematic views for explanation, and the number, thicknesses, sizes and the ratios of the sizes and the like of the patterns differ from reality.

Figure 4:
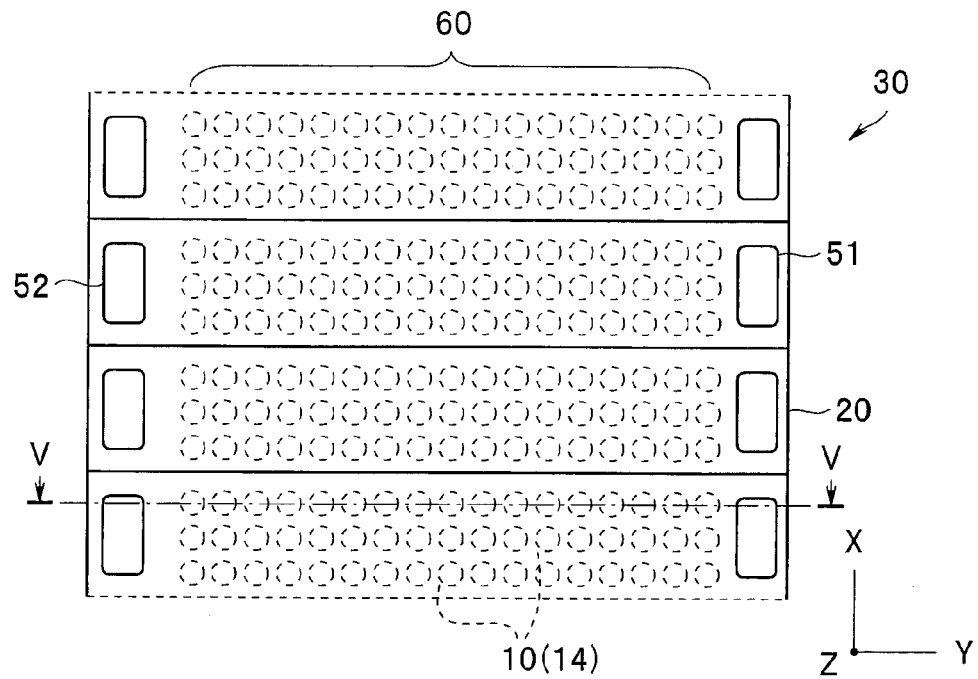
FIG. 4 is a top view for explaining a structure of an ultrasound element of the first embodiment.

As shown in FIG. 4, in the US elements 20, a plurality of electrostatic capacitance type US cells 10 are disposed in a matrix shape. Note that for explanation, only some of the US cells 10 are shown in FIG. 4. Disposition of the US cells 10 may be regular grid disposition, staggered disposition, triangular mesh disposition or the like, or may be random disposition. At one end portion of the US element 20, the lower electrode terminal 52 is placed, and at the other end portion, the upper electrode terminal 51 is placed.

Figure 5:
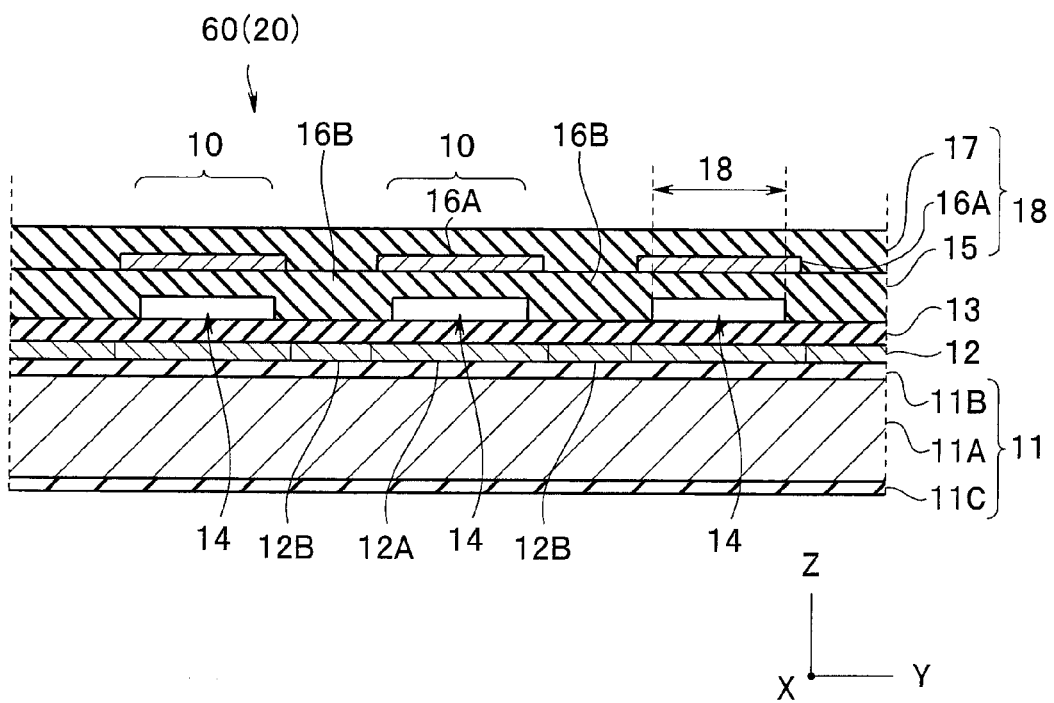
FIG. 5 is a partial sectional view taken along the V-V line of FIG. 4, for explaining the structure of the ultrasound element of the first embodiment.
Figure 6:
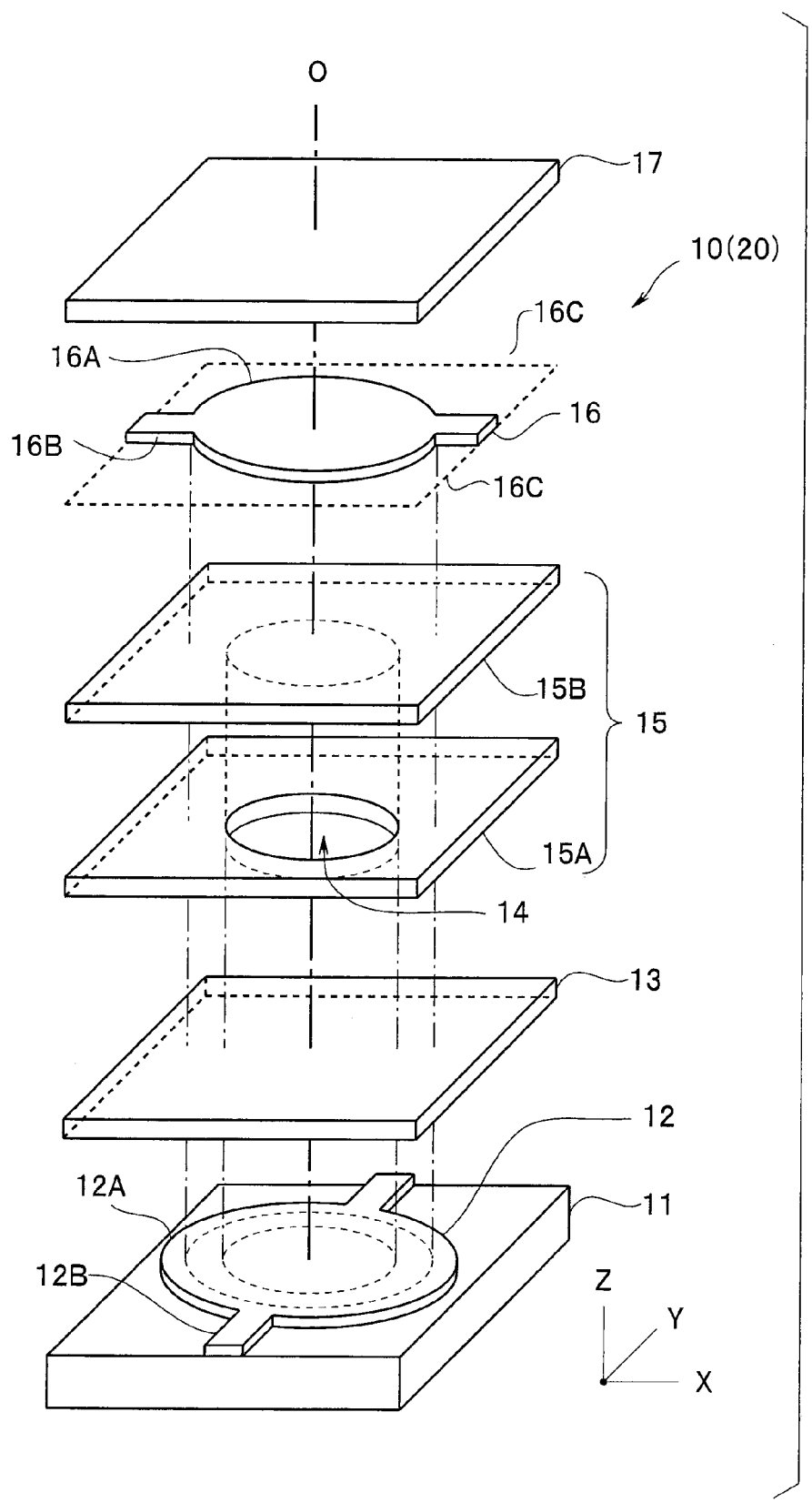
FIG. 6 is an exploded view for explaining a structure of an ultrasound cell of the first embodiment.

As shown in FIG. 5 and FIG. 6, a US cell 10 has, on a silicon substrate 11 that is a base substrate, a lower electrode layer 12 that is connected to the lower electrode terminal 52, a lower insulating layer (a first insulating layer) 13, an upper insulating layer (a second insulating layer) 15 in which cavities 14 in a cylindrical shape are formed, an upper electrode layer 16 that is connected to the upper electrode terminal 51, and a protection layer (a third insulating layer) 17, which are stacked in sequence. The silicon substrate 11 is a substrate in which silicon thermal oxide films 11B and 11C are formed on a surface of a silicon 11A.

Namely, the respective US cells 10 each have a lower electrode section 12A and an upper electrode section 16A that are disposed to face each other via the cavity 14.

The lower electrode layer 12 has a plurality of lower electrode sections 12A that are circular in plain view, and a plurality of lower wiring sections 12B that are provided extensively in two directions from edge side portions of the lower electrode sections 12A. The lower wiring sections 12B connect the lower electrode sections 12A of another US cell of the same US element 20. The lower wiring section 12B is connected to the lower electrode terminal 52.

The upper electrode layer 16 has a plurality of upper electrode sections 16A that are circular in plain view, and a plurality of upper wiring sections 16B that are provided extensively in two directions from edge side portions of the upper electrode sections 16A. The upper wiring sections 16B connect the upper electrode sections 16A of other US cells of the same US element 20. The upper wiring sections 16B are connected to the upper electrode terminals 51.

Namely, all the lower electrode sections 12A of a plurality of US cells 10 that are disposed in the same US element 20 are connected to one another, and all the upper electrode sections 16A are also connected to one another.

In the US cell 10 of the above described structure shown in FIG. 5 and FIG. 6, the upper insulating layer 15, the upper electrode layer 16 and the protection layer 17 in a region directly above the cavity 14 configure a membrane 18 that is a vibration section.

In the US cell 10, the cavity 14 is smaller than the lower electrode section 12A, and the upper electrode section 16A is smaller than the lower electrode section 12A and is larger than the cavity 14. Namely, a diameter R12 of the lower electrode section 12A, a diameter R14 of the cylindrical cavity 14, and a diameter R16 of the upper electrode section 16A all of which are in circle shapes in plain view are in the relation of the following (expression 1).

$$R12 > R16 > R14 \quad \text{(expression 1)}$$

The lower electrode section 12A, the cavity 14 and the upper electrode section 16A are placed in such a manner that centers of the respective circles correspond to a center line O that is perpendicular to the silicon substrate 11.

Note that a section in which the lower electrode section 12A and the upper electrode section 16A are disposed to face each other via the cavity 14 is a variable capacitance section CE in which an electrostatic capacitance changes at a time of reception of ultrasound.

<Action of US Element>

Figure 7:
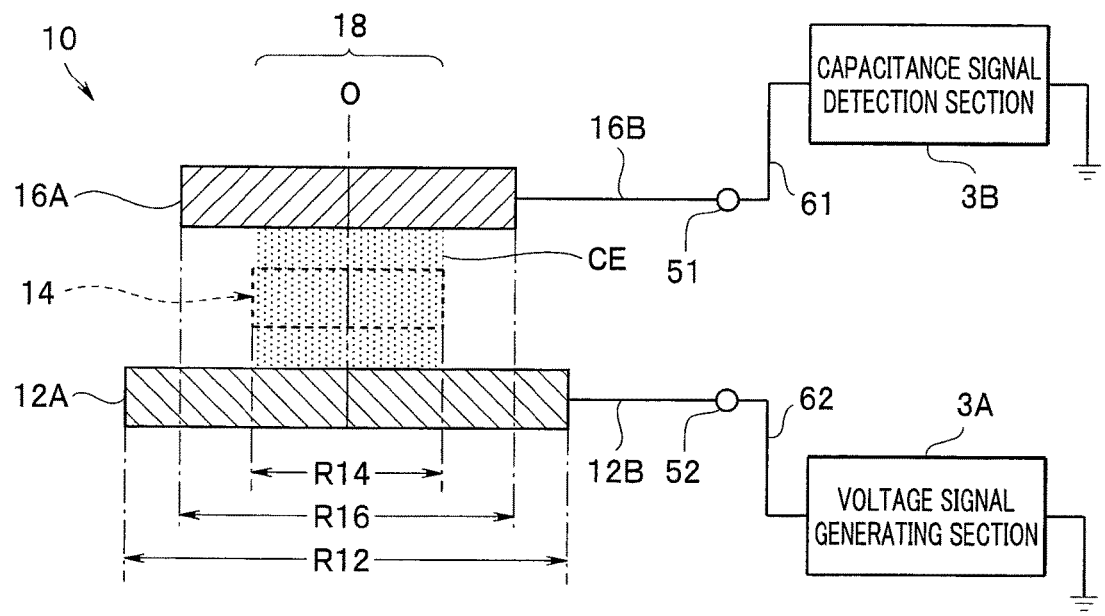
FIG. 7 is a schematic view for explaining an action of the ultrasound cell of the first embodiment.

Next, with use of FIG. 7, an action of the US element 20 will be described. The lower electrode section 12A is connected to a voltage signal generating section 3A of the ultrasound observation apparatus 3 via the lower electrode terminal 52. On the other hand, the upper electrode section 16A is connected to a capacitance signal detection section 3B via the upper electrode terminal 51 to be at a ground potential. The capacitance signal detection section 3B detects a capacitance signal (current change).

At a time of generation of ultrasound, the voltage signal generating section 3A applies a drive voltage signal to the lower electrode section 12A. When the voltage is applied to the lower electrode section 12A, the upper electrode section 16A at the ground potential is drawn to the lower electrode section 12A by an electrostatic force, and therefore, the membrane 18 that includes the upper electrode section 16A deforms. Subsequently, when voltage application to the lower electrode section 12A is eliminated, the membrane 18 is restored to an original shape by an elastic force. By deformation/restoration of the membrane 18, ultrasound is generated.

On the other hand, at the time of reception of ultrasound; the membrane 18 including the upper electrode section 16A is deformed by the received ultrasound energy. Thereupon, a distance between the upper electrode section 16A and the lower electrode section 12A changes, and therefore, the electrostatic capacitance therebetween also changes. Then, a current accompanying the capacitance change flows to the capacitance signal detection section 3B. Namely, the received ultrasound energy is converted into a capacitance signal.

<Stacking Misalignment>

As already described, in the US cell 10, the cavity 14 is formed at an upper side of the plurality of lower electrode sections 12A so that the center line O is shared, and further on an upper side of the cavity 14, the upper electrode section 16A is formed so that the center line O is shared.

Figure 8:
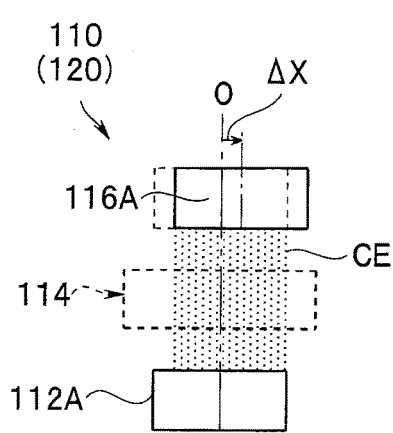
FIG. 8 is a schematic view for explaining stacking misalignment of an ultrasound cell of a comparative example.

However, in a manufacturing process, stacking misalignment, namely, stacking formation is not sometimes performed in a correct position. For example, a US cell 110 of a comparative example shown in FIG. 8, sizes of an upper electrode section 116A and a lower electrode section 112A are smaller than that of a cavity 114. If stacking misalignment (pattern misalignment of 0.5 μm, for example) occurs at a time of formation of the upper electrode section 116A, the variable capacitance section CE becomes small in the US cell 110. Then, sensitivity of the US cell 110 declines. A degree of stacking misalignment results from manufacturing variation, and therefore, characteristics of a US element 120 are unstable.

Figure 9:
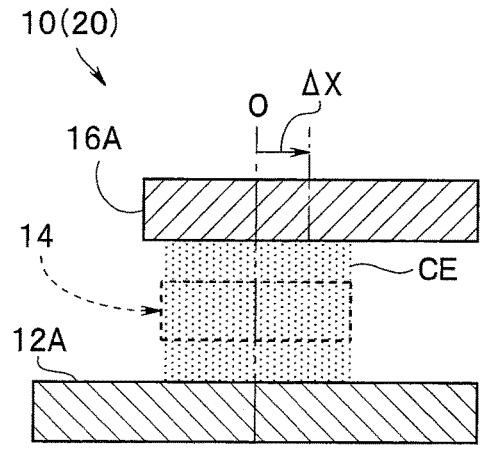
FIG. 9 is a schematic view for explaining stacking misalignment of the ultrasound cell of the first embodiment.

In contrast with the above, as shown in FIG. 9, in the US cell 10 of the present embodiment, even if stacking misalignment of, for example, 0.5 μm occurs at the time of formation of the upper electrode section 16A, the size of the variable capacitance section CE does not change. Therefore, even if there is a manufacturing variation, the characteristics of the US element 20 and the US endoscope 2 are stable.

As already described, if "the diameter R12 of the lower electrode section 12A>the diameter R16 of the upper electrode section 16A>R14 of the cavity 14" is satisfied, the above described effect is provided. In particular, in the present technical level, the variation (stacking misalignment) at the time of manufacturing is several μm, for example, 0.5 to 5 μm, and therefore, "R12=R16+(0.5 to 5 μm), R16=R14+(0.5 to 5 μm)" is preferable. Alternatively, "R12=R16×(1.03 to 1.10), R16=R14×(1.03 to 1.10)" is preferable.

Within the above described range, the size of the variable capacitance section CE does not change even if stacking misalignment due to a manufacturing variation occurs, and therefore, the characteristics of the US element 20 and the US endoscope 2 are stable.

<Parasitic Capacitance between Wiring Sections>

Figure 10:
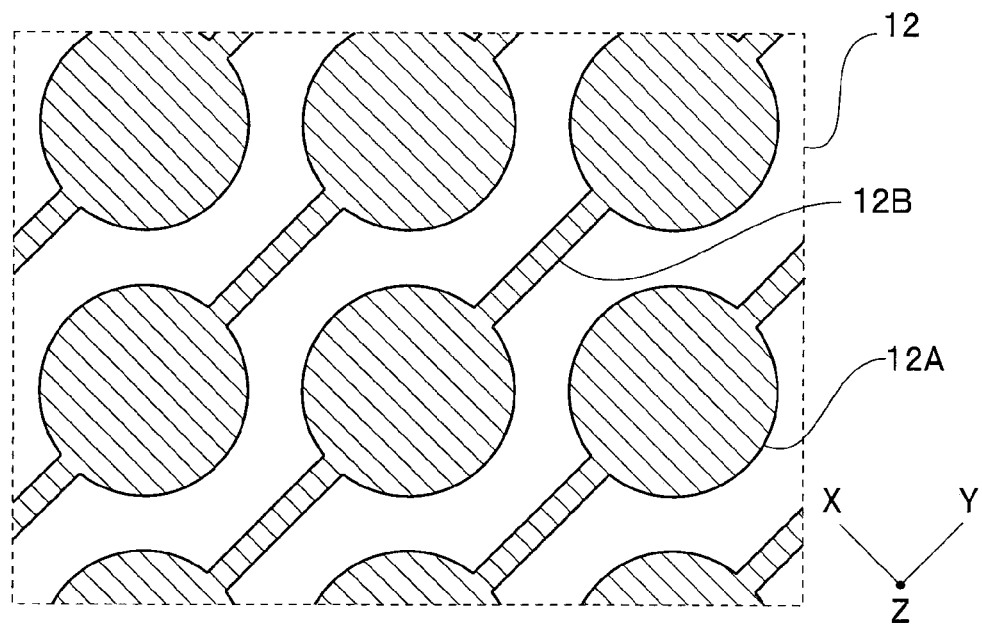
FIG. 10 is a top view showing a pattern of a lower electrode layer of an ultrasound element of a second embodiment.
Figure 11:
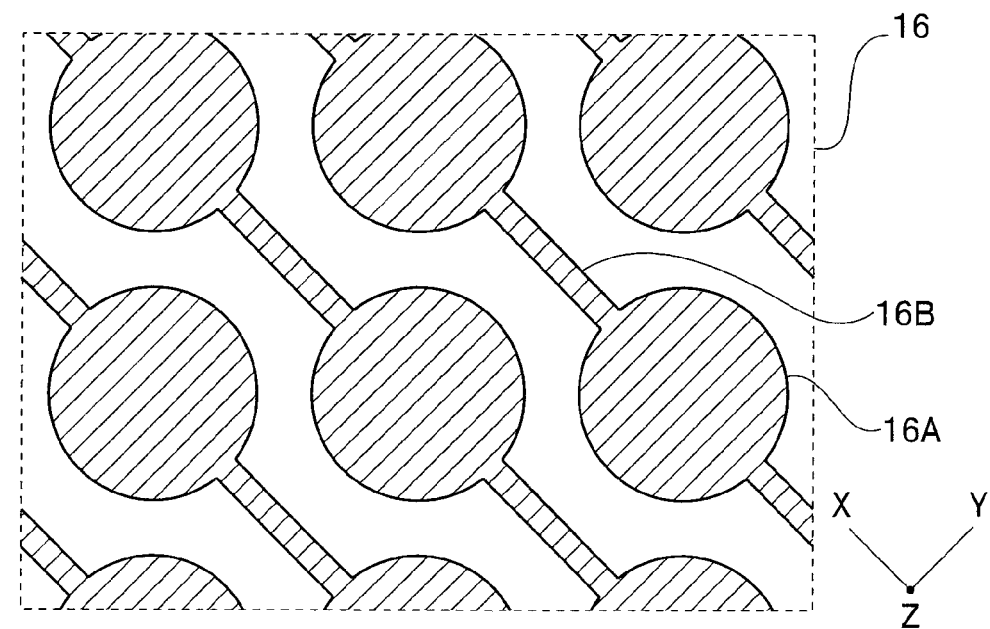
FIG. 11 is a top view showing a pattern of an upper electrode layer of the ultrasound element of the second embodiment.

Further, as shown in FIG. 6 and the like, the lower wiring section 12B and the upper wiring section 16B in longitudinal directions thereof of the US element 20 are orthogonal to each other. Namely, as shown in FIG. 10, the lower wiring section 12B is provided extensively in a Y axis direction from the lower electrode section 12A, whereas as shown in FIG. 11, the upper wiring section 16B is provided extensively in an X axis direction from the upper electrode section 16A.

Here, in the US element 20, the electrostatic capacitance that is detected by the capacitance signal detection section 3B is a total of the electrostatic capacitance and a parasitic capacitance of the variable capacitance section CE that is already described. Here, the parasitic capacitance refers to an electrostatic capacitance of a capacitance fixation section, which does not change even if deformation of the membrane 18 occurs. For example, when the lower wiring section 12B and the upper wiring section 16B are disposed to face each other, a parasitic capacitance is generated therebetween.

In contrast with the above, in the US element 20 in which the upper wiring section 16B and the lower wiring section 12B are placed in directions orthogonal to each other so as not to be disposed to face each other, a parasitic capacitance does not occur between the upper wiring section 16B and the lower wiring section 12B, and therefore, reception sensitivity of ultrasound is high.

Second Embodiment

Next, a US element 20A and an ultrasound endoscope 2A that includes the US element 20A of a second embodiment will be described. Since the US element 20A and the US endoscope 2A are analogous to the US element 20 and the US endoscope 2, the same components are assigned with the same reference, signs, and explanation thereof will be omitted.

Figure 12:
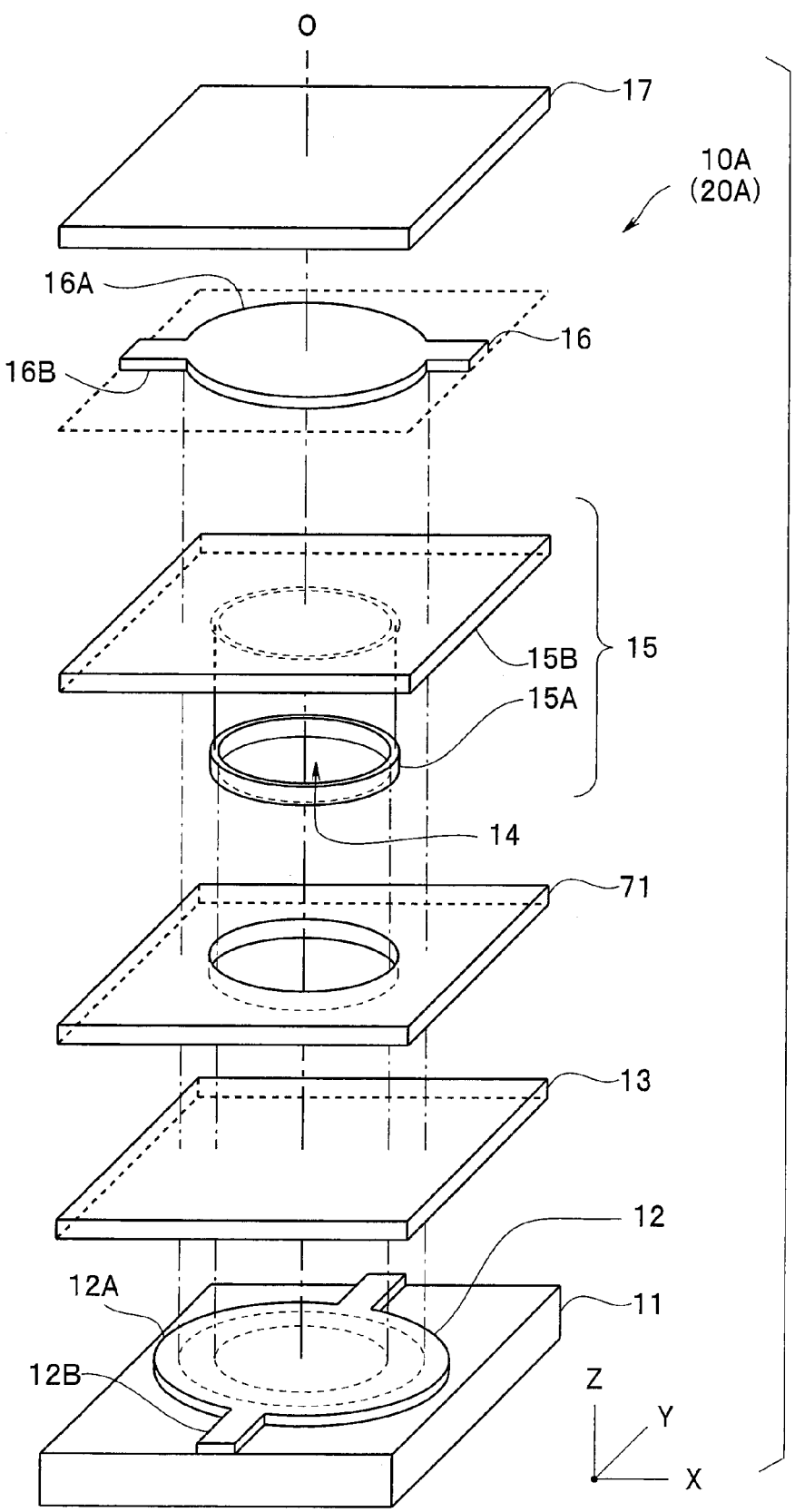
FIG. 12 is an exploded view for explaining a structure of an ultrasound cell of the second embodiment.

As shown in FIG. 12, a US cell 10A of the US element 20A includes a shield electrode section 71 on an outer circumferential portion of the cavity 14 including a region in which an outer circumferential portion of the lower electrode section 12A and an outer circumferential portion of the upper electrode section 16A are disposed to face each other. As will be described later, the cavity 14 is a region in which a sacrificial layer 70 which is formed by a conductive material and covered with the upper insulating layer 15 is partially removed by an etching process, and the shield electrode section 71 is a remaining region of the sacrificial layer 70 that is not removed by the etching process. The shield electrode section 71 is connected to the shield electrode terminal 53 at the ground potential.

<Manufacturing Method of US Element 20A>

Next, with use of FIG. 13A to FIG. 13F, FIG. 14 and FIG. 15, a manufacturing method of the US element 20A will be briefly described. Note that a manufacturing method of the US element 20 that is already described is substantially the same except for production of the shield electrode section 71.

<Step S11> Formation of the Lower Electrode Layer

A conductive material made of conductive silicon or a metal, for example, copper, gold or aluminum is deposited on an entire surface of the silicon substrate 11 by a sputtering method or the like. Subsequently, a mask pattern is formed by photolithography, and thereafter, is partially removed by etching, whereby the lower electrode layer 12 that has the lower electrode section 12A and the lower wiring section 12B is formed.

<Step S12> Formation of the Lower Insulating Layer

The lower insulating layer 13 formed of an insulating material such as SiN is deposited by, for example, a CVD method (a chemical vapor deposition method) in such a manner as to cover the lower electrode layer 12.

<Step S13> Formation of the Sacrificial Layer

Figure 13A:
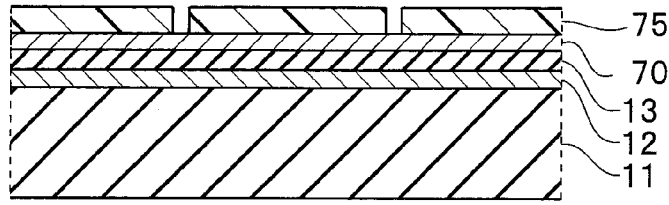
FIG. 13A is a sectional view for explaining a manufacturing method of the ultrasound cell of the second embodiment.

On the lower insulating layer 13, a sacrificial layer material formed of a material that is selected from conductive materials and is removable by etching is deposited. Subsequently, a mask pattern 75 by photolithography is formed on the sacrificial layer 70 as shown in FIG. 13A.

<Step S14> Sacrificial Layer Patterning

Figure 13B:
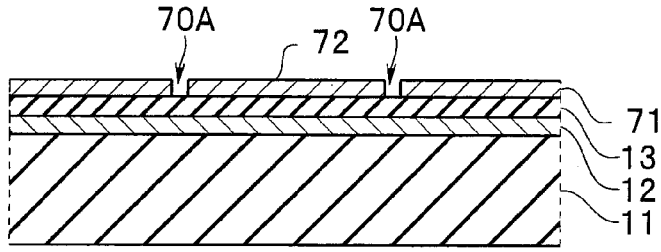
FIG. 13B is a sectional view for explaining the manufacturing method of the ultrasound cell of the second embodiment.
Figure 14:
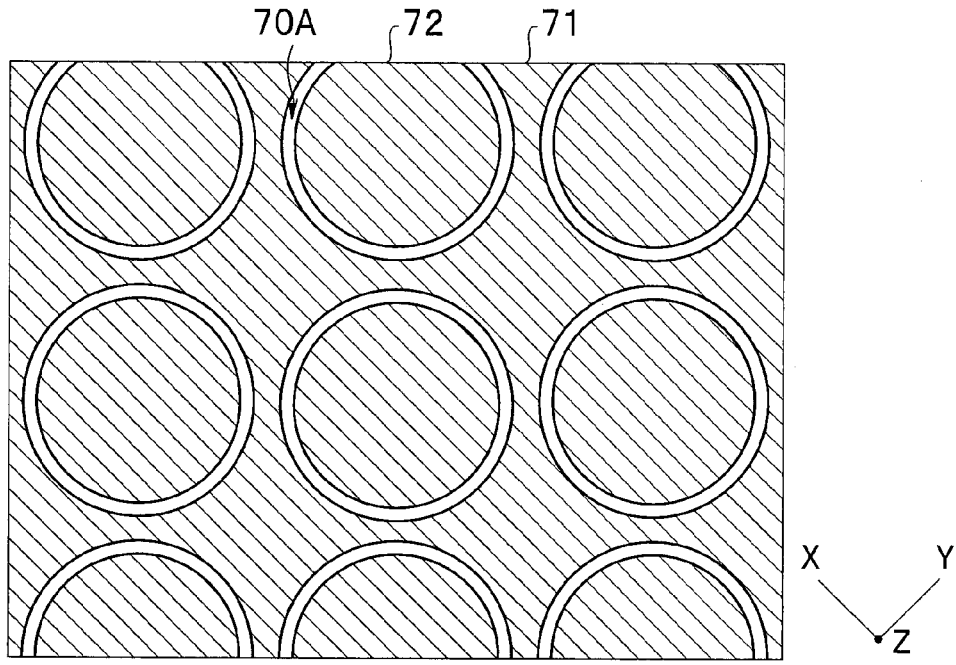
FIG. 14 is a top view showing a pattern of a sacrificial layer of the ultrasound cell of the second embodiment.

As shown in FIG. 13B and FIG. 14, the sacrificial layer 70 is divided into a cavity section 72 in a shape of a cavity (columnar shape) and the shield electrode section 71 via a doughnut-shaped groove section 70A by an etching process.

Since a thickness of the sacrificial layer 70 corresponds to a height of the cavity 14, and therefore, is, for example, 0.05 to 0.3 µm, and is preferably 0.05 to 0.15 µm.

<Step S15> Formation of the Upper Insulating Layer

Figure 13C:
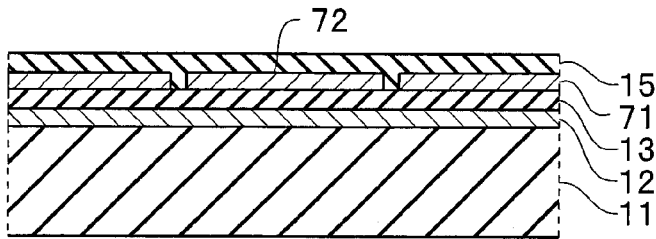
FIG. 13C is a sectional view for explaining the manufacturing method of the ultrasound cell of the second embodiment.

As shown in FIG. 13C, on a top surface of the sacrificial layer pattern (the cavity section 72 and the shield electrode section 71), the upper insulating layer 15 is formed by the method and the material similar to those for the lower insulating layer 13, for example. At this time, the upper insulating layer 15A is also formed in an inside of the groove section 70A, as already described.

Here, the upper insulating layer 15 is formed to cover the sacrificial layer pattern, and therefore, irregularities may occur due to the influence of the thickness of the sacrificial layer pattern. Then, insulation of the upper electrode layer that is formed on the upper insulating layer and the lower electrode layer is worsened, and action of the US cell sometimes becomes unstable.

Therefore, after the upper insulating layer is formed, a surface thereof is preferably subjected to planarization. For planarization, for example, a chemical mechanical polishing method (CMP method) can be preferably used.

The US element in which the top surface of the upper insulating layer is flat has stable characteristics.

Subsequently, in a predetermined position of the upper insulating layer 15, an opening portion (not illustrated) in which an etching agent is poured is formed in order to remove the cavity section 72.

<Step S16> Formation of the Cavity (Formation of the Shield Electrode Section)

Figure 13D:
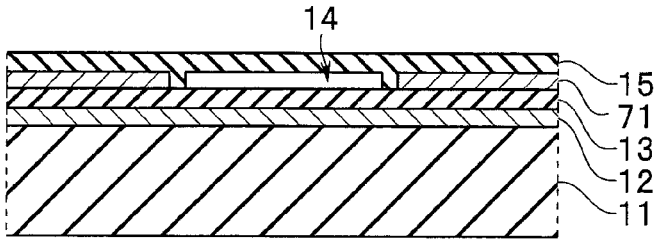
FIG. 13D is a sectional view for explaining the manufacturing method of the ultrasound cell of the second embodiment.
Figure 15:
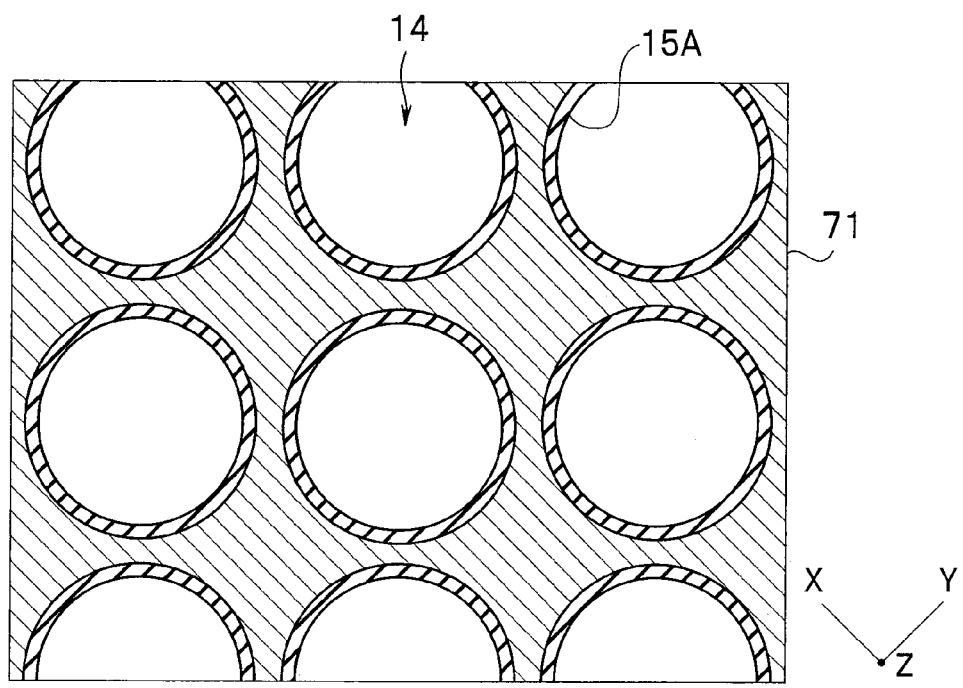
FIG. 15 is a top view showing a pattern of a shield electrode section of the ultrasound cell of the second embodiment.

Next, as shown in FIG. 13D and FIG. 15, the cavity 14 is formed by removal of the cavity section 72 by etching. The shield electrode section 71 is separated from the cavity section 72 by the upper insulating layer 15A, and therefore, is not removed by the etching agent. Namely, the shield electrode section 71 is the remaining region of the sacrificial layer 70 that is not removed by the etching process.

For example, when tungsten (W) is used as the sacrificial layer 70, and silicon nitride (SiN) is used as the lower insulating layer 13 and the upper insulating layer 15, a hydrogen peroxide solution ($H_2O_2$) is used as the etching agent. Further, when conductive polycrystalline silicon is used as the sacrificial layer 70, and SiN is used as the lower insulating layer 13 and the upper insulating layer 15, xenon difluoride gas ($XeF_2$) is used as the etching agent.

Note that the cavity 14 is not limited to being in a columnar shape, but may be in a polygonal column shape or the like. When the cavity 14 is in a polygonal column shape, the shapes in plain view of the upper electrode section 16A and the lower electrode section 12A are also preferably formed into polygonal shapes.

Further, when the shapes in plain view are not circular, the patterns of the upper electrode section 16A and the like can be in such sizes that a large pattern can contain a small pattern.

<Step S17> Formation of the Upper Electrode Layer

Figure 13E:
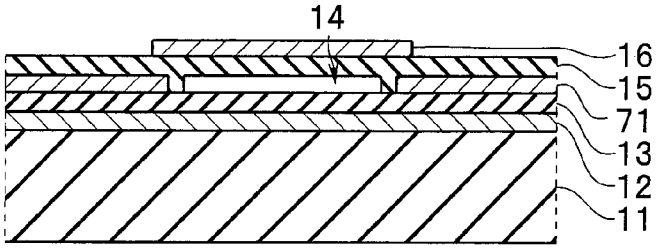
FIG. 13E is a sectional view for explaining the manufacturing method of the ultrasound cell of the second embodiment.

As shown in FIG. 13E, by the method and the material similar to those for the lower electrode layer 12, the upper electrode layer 16 that has the upper electrode section 16A and the upper wiring section 16B is formed.

<Step S18> Formation of the Protection Layer

Figure 13F:
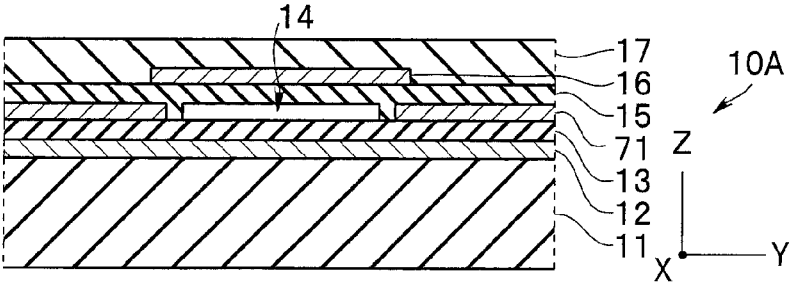
FIG. 13F is a sectional view for explaining the manufacturing method of the ultrasound cell of the second embodiment.

As shown in FIG. 13F, the surface of the US element 20 is covered with the protection layer 17. The protection layer 17 has not only a protection function, but also a sound matching layer function, and a function of connecting the US element 20.

Note that though explanation is omitted, the lower electrode terminal 52 is also formed in the lower electrode forming step, the upper electrode terminal 51 is also formed in the upper electrode forming step, and the shield electrode terminal 53 is also formed in the shield electrode forming step (sacrificial layer formation). The protection layer 17 is formed so as not to cover the lower electrode terminal 52, the upper electrode terminal 51 and the shield electrode terminal 53.

The protection layer 17 is formed of a flexible resin such as polyimide, epoxy, acryl or poly-para-xylene, and is especially preferably formed of polyimide, because polyimide has high chemical resistance, has a curving property, and is easy to process. Note that the protection layer 17 may have a two-layer structure in which a second insulating layer having biocompatibility is further formed on a first insulating layer.

Next, a plurality of ultrasound elements 20 are roundly disposed in a radial shape with a predetermined diameter in a connecting direction, whereby the US array 40 is produced. For example, the US array 40 is joined to an outer periphery of a cylinder with a predetermined diameter, for example. Further, the coaxial cable bundle 35 is connected to the US array 40, and the US unit 30 is produced.

<Action of US Element 20A>

Figure 16:
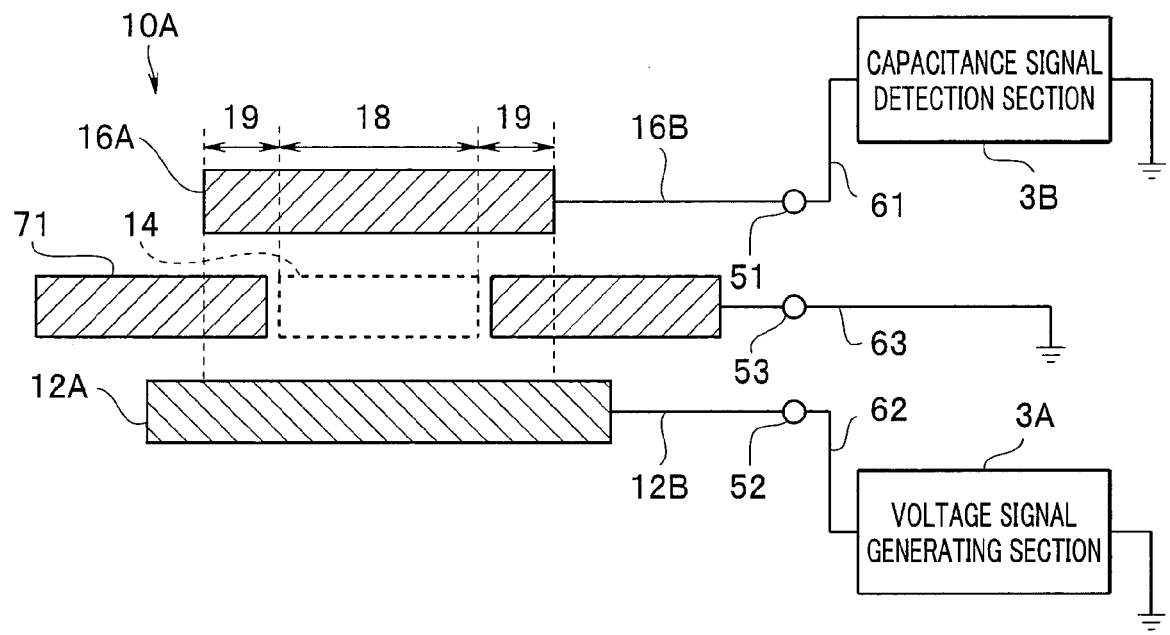
FIG. 16 is a schematic view for explaining an action of the ultrasound cell of the second embodiment.

Next, with use of FIG. 16, an action of the US element 20A will be described. The lower electrode section 12A is connected to the voltage signal generating section 3A of the ultrasound observation apparatus 3 via the lower electrode terminal 52. The shield electrode section 71 is at the ground potential via the shield electrode terminal 53. On the other hand, the upper electrode section 16A is connected to the capacitance signal detection section 3B via the upper electrode terminal 51 to be at the ground potential. The capacitance signal detection section 3B detects a capacitance signal (current change).

However, in the US element 20, there is a part where the lower electrode section 12A and the upper electrode section 16A are disposed to face each other, in an outer circumferential region of the membrane 18. The facing portion forms a capacitor, and is a parasitic capacitance section (fixed capacitance section) 19 in which an electrostatic capacitance does not change even when ultrasound is received. When the electrostatic capacitance of the parasitic capacitance section 19 is large, even if the electrostatic capacitance of the membrane 18 (variable capacitance section) changes, a change rate of the capacitance signal (electrostatic capacitance) that is detected in the capacitance signal detection section 3B becomes small.

Here, in the US element 20A, the shield electrode section 71 at the ground potential is placed on the outer circumferential portion where the lower electrode section 12A and the upper electrode section 16A are disposed to face each other. Therefore, the upper electrode section 16A on the part where the lower electrode section 12A and the shield electrode section 71 are disposed to face each other does not form a capacitor with the lower electrode section 12A. Namely, the outer circumferential portion of the upper electrode section 16A does not become a cause of a parasitic capacitance. Therefore, the US element 20A has higher reception sensitivity of ultrasound than that of the US element 20 that does not have the shield electrode section 71.

Further, the shield electrode section 74 is formed by the sacrificial layer 70, and therefore, increase in the number of steps is small, and manufacture is easy.

Furthermore, even if a part of the insulating film is broken due to dust, a defect or the like in the US element 20A, the upper side of the lower wiring section 12B is covered with the shield electrode section 74 at the ground potential. Therefore, a voltage signal (a drive signal and a bias signal) that is applied to the lower wiring section 12B does not leak outside the US element 20A. Therefore, the characteristics of the US element 20A and the US endoscope 2A are further stable.

Third Embodiment

Next, a US element 20B and an ultrasound endoscope 2B including the US element 20B of a third embodiment will be described. Since the US element 20B and the US endoscope 2B are analogous to the US element 20 and the US endoscope 2, the same components will be assigned with the same reference signs, and explanation thereof will be omitted.

Figure 17:
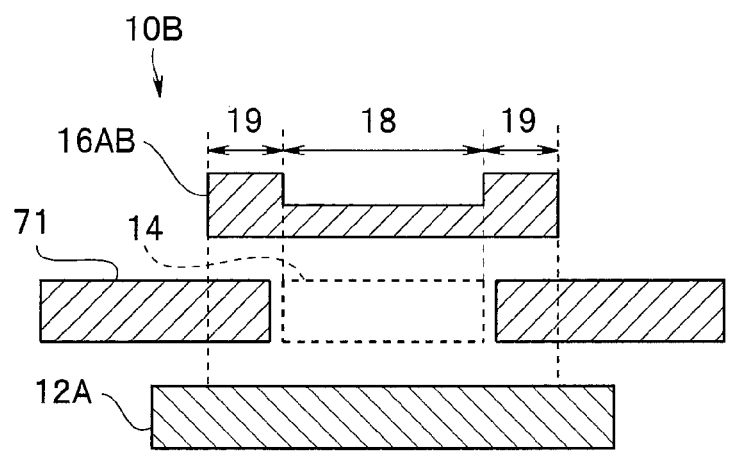
FIG. 17 is a sectional view for explaining a structure of an ultrasound cell of a third embodiment.

As shown in FIG. 17, in the US element 20B, the upper electrode section 16A has a thickness of a central portion smaller than a thickness of the outer peripheral portion. Here, the outer circumferential portion refers to a region that does not configure a membrane. Note that a thickness of the upper wiring section 16B is preferable the same thickness as the outer circumferential portion of the upper electrode section 16A.

When the thickness of the central portion of the upper electrode section 16A that configures the membrane 18 is small, the membrane 18 easily vibrates, and therefore, the US element 20B having US cells 10B and the US endoscope 2B are highly sensitive.

Note that the thickness of the upper electrode section 16A may be gradually thinner toward the central portion from the outer circumferential portion. Further, the upper electrode section 16A that configures the membrane 18 may have a number of concave portions or through-holes. Namely, the thickness may be an average film thickness.

The present invention is not limited to the embodiments described above, and various modifications, alterations and the like can be made within the range without changing the gist of the present invention.

What is claimed is:

1. An ultrasound element, comprising:
   a base substrate;
   a lower electrode layer that has a plurality of lower electrode sections, and a plurality of lower wiring sections that connect the plurality of lower electrode sections, and is connected to a lower electrode terminal to which a drive signal and a bias signal are applied;
   a lower insulating layer;
   an upper insulating layer in which a plurality of cavities smaller than the respective lower electrode sections are formed;
   an upper electrode layer that has a plurality of upper electrode sections that are disposed to face the respective lower electrode sections via the respective cavities, and are smaller than the lower electrode sections and larger than the cavities, and a plurality of upper wiring sections that connect the plurality of upper electrode sections, and is connected to an upper electrode terminal at a ground potential that detects a capacitance signal; and a protection layer, wherein the upper wiring sections and the lower wiring sections are placed so as not to be disposed to face each other, and wherein the ultrasound element further comprises:

a shield electrode section that is disposed on entire outer circumferential portions of the cavities that include a region where outer circumferential portions of the lower electrode sections and outer circumferential portions of the upper electrode sections are disposed to face each other, the shield electrode section being connected to a shield electrode terminal at the ground potential.

2. The ultrasound element according to claim 1, wherein the cavities are regions where a sacrificial layer that is covered with the upper insulating layer and is formed of a conductive material is partially removed by an etching process, and the shield electrode section is a remaining region of the sacrificial layer that is not removed by the etching process.

3. The ultrasound element according to claim 2, wherein a top surface of the upper insulating layer is flat.

4. The ultrasound element according to claim 3, wherein in the upper electrode sections, a thickness of a central portion is smaller than a thickness of the outer circumferential portion.

5. An ultrasound endoscope, comprising:

a base substrate;

a lower electrode layer that has a plurality of lower electrode sections, and a plurality of lower wiring sections that connect the plurality of lower electrode sections, and is connected to a lower electrode terminal to which a drive signal and a bias signal are applied;

a lower insulating layer;

an upper insulating layer in which a plurality of cavities smaller than the respective lower electrode sections are formed;

an upper electrode layer that has a plurality of upper electrode sections that are disposed to face the respective lower electrode sections via the respective cavities, and are smaller than the lower electrode sections and larger than the cavities, and a plurality of upper wiring sections that connect the plurality of upper electrode sections, and is connected to an upper electrode terminal at a ground potential that detects a capacitance signal; and a protection layer;

wherein the upper wiring sections and the lower wiring sections are placed so as not to be disposed to face each other, and wherein the ultrasound endoscope further comprises:

a shield electrode section that is disposed on entire outer circumferential portions of the cavities that include a region where outer circumferential portions of the lower electrode sections and outer circumferential portions of the upper electrode sections are disposed to face each other, the shield electrode section being connected to a shield electrode terminal at the ground potential.

6. The ultrasound endoscope according to claim 5, wherein the cavities are a region where a sacrificial layer that is covered with the upper insulating layer and is formed of a conductive material is partially removed by an etching process, and the shield electrode section is a remaining region of the sacrificial layer that is not removed by the etching process.

7. The ultrasound endoscope according to claim 6, wherein a top surface of the upper insulating layer is flat.

8. The ultrasound endoscope according to claim 7, wherein in the upper electrode sections, a thickness of a central portion is smaller than a thickness of the outer circumferential portion.

* * * * *